United States Patent
Hamad et al.

(10) Patent No.: US 10,368,959 B2
(45) Date of Patent: Aug. 6, 2019

(54) DENTAL HANDPIECE COMPRISING A PELTIER ELEMENT OR THERMO-ELECTRIC COOLER TO COOL THE DENTAL BURR

(71) Applicants: Abuhaimed Hamad, Geneva (CH); Ivo Krejci, Commugny (CH)

(72) Inventors: Abuhaimed Hamad, Geneva (CH); Ivo Krejci, Commugny (CH)

(73) Assignee: Abuhaimed Hamad (CH)

(*) Notice: Subject to any disclaimer, the term of this patent is extended or adjusted under 35 U.S.C. 154(b) by 0 days.

(21) Appl. No.: 15/740,886

(22) PCT Filed: Jul. 2, 2015

(86) PCT No.: PCT/IB2015/001100
§ 371 (c)(1),
(2) Date: Dec. 29, 2017

(87) PCT Pub. No.: WO2017/001879
PCT Pub. Date: Jan. 5, 2017

(65) Prior Publication Data
US 2018/0185116 A1 Jul. 5, 2018

(51) Int. Cl.
*A61C 1/06* (2006.01)
*A61C 1/00* (2006.01)
*A61C 1/14* (2006.01)
*H01L 35/28* (2006.01)

(52) U.S. Cl.
CPC .............. *A61C 1/0069* (2013.01); *A61C 1/06* (2013.01); *A61C 1/141* (2013.01); *H01L 35/28* (2013.01); *A61C 1/0023* (2013.01); *A61C 2204/005* (2013.01)

(58) Field of Classification Search
CPC ............ A61C 1/0069; A61C 1/06; A61C 1/14; A61C 1/141; A61C 1/145
See application file for complete search history.

(56) References Cited

U.S. PATENT DOCUMENTS 4,661,060 A * 4/1987 Strohmaier .............. A61C 1/06
433/126
4,975,056 A * 12/1990 Eibofner ............ A61B 17/1646
433/115

(Continued)

FOREIGN PATENT DOCUMENTS

EP          0743029      11/1996
JP          2001321391    11/2001

*Primary Examiner* — Ralph A Lewis
(74) *Attorney, Agent, or Firm* — Galbreath Law Offices, P.C.; John A. Galbreath

(57) ABSTRACT

A dental handpiece comprises an outer sleeve (1), a tool-holding socket (2) for holding a treatment tool (3) arranged in the handpiece, wherein the tool-holding socket (2) has a central axis about which the tool-holding socket (2) can be rotated and/or oscillated and wherein the tool-holding socket (2) is arranged to be driven by a driveshaft of the handpiece driven by a motor (10) housed in the outer sleeve (1). At least one Peltier element (5) is received in the handpiece in thermal contact with the tool-holding socket (2), the Peltier element (5) having a cool face in thermal contact with the tool-holding socket (2) to cool a treatment tool (3) held therein when the tool (3) is driven in rotation or oscillation.

13 Claims, 1 Drawing Sheet

(56) References Cited

U.S. PATENT DOCUMENTS

Figure 1:
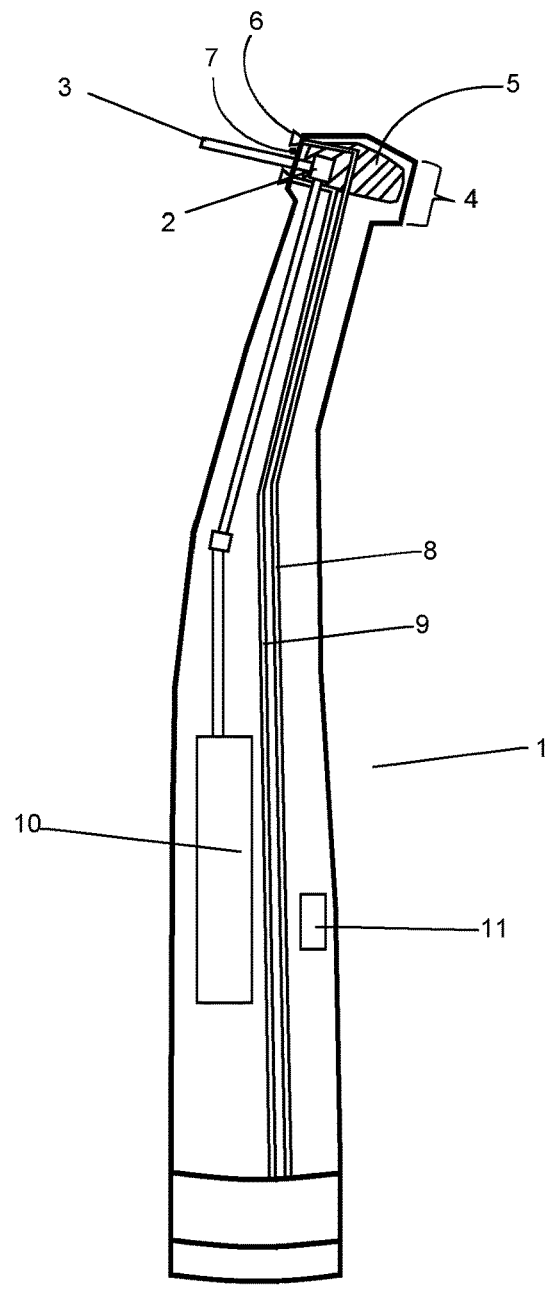

| | | | | |
|---|---|---|---|---|
| 5,658,148 A | * | 8/1997 | Neuberger | A46B 15/0002 424/49 |
| 6,196,839 B1 | * | 3/2001 | Ross | A61C 3/00 433/3 |
| 7,645,056 B1 | * | 1/2010 | Mills | A61C 19/004 165/104.19 |
| 2014/0072930 A1 | | 3/2014 | Pruckner | |
| 2018/0185116 A1 | * | 7/2018 | Hamad | A61C 1/141 |

* cited by examiner

DENTAL HANDPIECE COMPRISING A PELTIER ELEMENT OR THERMO-ELECTRIC COOLER TO COOL THE DENTAL BURR

The present invention relates to a dental handpiece, and more particularly, to a dental handpiece incorporating a cooling system.

Dental handpieces are generally used to perform both grinding and cutting operations upon a workpiece. Either of these operations generate a substantial amount of heat. Where workpieces are tooth, bone and/or filling within a tooth in a patient mouth, the heat generated may be painful as well as uncomfortable. Where the dental handpiece is used upon workpieces outside of a patients mouth, such as braces, dentures, and splints, the heat generated may deleteriously affect the materials being worked upon.

To circumvent the problems attendant the generated heat, various means have been developed to reduce or dissipate the generated heat. In one type of an air driven handpiece, water is pumped through the dental handpiece, into a hollow burr and flows from the working portion thereof onto the workpiece. The use of water is satisfactory in several respects in that it is easily obtainable, requires no special containers and does not quickly corrode the working elements of the dental handpiece if properly channeled. However, two major problems exist when water is used. First, the channeling of the water from the dental handpiece and into the hollow burr requires specially designed elements to prevent the water from entering the bearings supporting the rotating burr and removing or limiting the effectiveness of the bearing lubricant. Second, although the water does not usually affect the properties of the workpiece. the presence of water, whether in liquid form or as a mist, tends to obscure the workpiece from view. Thereby, the amount of work that can be performed by the burr is limited by required periodic mopping or draining of the water. The lubricant, such as water, may be the source of bacterial contamination of the operating field and of the inner water containing parts of the handpiece which are almost impossible to clean and thus to sterilize.

Electric motor driven dental handpieces are described for example in U.S. Pat. No. 4,278,429 and in U.S. Pat. No. 4,355,977. In some aspects, electric powered handpieces have advantages over air powered models, for example, electric powered handpieces exhibit superior speed regulation; provide an acceptable degree of speed regulation over a wide range of desired outputs speeds and the torque that is supplied, particularly at lower speeds, is excellent. However, electrical powered handpiece have disadvantages likened to air driven handpieces, including scarcity of cooling system, heavy weight, lack of rinsing and connective cable for electricity, water and air.

In 1993, CDC (Centers for Disease Control and Prevention) recommended that dental waterlines be flushed at the beginning of the clinic day to reduce the microbial load. However, studies have demonstrated this practice does not affect biofilm in the waterlines or reliably improve the quality of water used during dental treatment. Dental unit water that remains untreated or unfiltered is unlikely to meet drinking water standards, <500 CFU/mL, therefore, one or more commercial devices and procedures designed to improve the quality of water should be employed. At the present time, commercially available options for improving dental unit water quality include the use of: Independent water reservoirs, chemical treatment regimens source water treatment systems, daily draining and air purging regimens and point-of-use filters.

Water and spray (water/air mixture) cooling is an integral component of a modern DCU (Dental Care Unit). For example high-speed micromotors require sufficient water-cooling, whereby a fine aerosol is also created. Although suction systems reduce aerosol formation, saliva and micro-organisms from the mouth still reach the system. Reducing backflow of contaminated water is a real problem. Furthermore, humidity of the suction system and connecting tubes provide optimal conditions for the growth of microorganisms which can develop into resistant biofilms and attach themselves to the insides of the tubes.

The present invention relates to a dental handpiece comprising a cooling system which decreases the risks associated with the growth of the bacteria.

According to the invention, a dental handpiece comprises an outer sleeve, a tool-holding socket for holding a treatment tool arranged in the handpiece. The tool-holding socket has a central axis about which the tool-holding socket can be rotated and/or oscillated. The tool-holding socket is arranged to be driven by a driveshaft of the handpiece driven by a motor housed in the outer sleeve. At least one Peltier element is received in the handpiece in thermal contact with the tool-holding socket, the Peltier element having a cool face in thermal contact with the tool-holding socket to cool a treatment tool held therein when the tool is driven in rotation or oscillation.

In one embodiment, the motor is an electric motor driven by a power supply and/or a battery.

Preferably, the dental handpiece comprises at least two tubes external or internal to the outer sleeve, one for lubricant and the other one for compressed gas or for pumped liquid/gas.

In one embodiment, the dental handpiece comprises a wireless receiver for a wireless connection with an external control for example a foot pedal containing a transmitter, or a PC, or a smart phone, a smart tablet, a PC, or a laptop.

Optionally, the outer sleeve of the dental handpiece body is made with a resistant surface coating.

In another embodiment, the tool-holding socket comprises a detachable handpiece shank and head adaptable to the dental treatment requirements.

In a preferred embodiment, the wireless dental handpiece comprises a thermal insulation material covering the entire surface of a handpiece body.

In another embodiment, the dental handpiece includes a micro cryocooler and/or micro gas circulation within the handpiece body for cooling purposes.

In one embodiment, the tool-holding socket, the Peltier element(s) and optionally a light source are located in a tip portion of the handpiece.

In another embodiment, the dental handpiece comprises a fixed and/or removable screen. This small screen can be used to show the status of the handpiece for instance, the battery status, the speed, the lubricant flow . . . . The screen can be arranged on the body of the handpiece.

Figure 2:
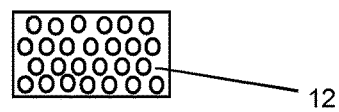

The invention will be more clearly understood from the following description of a preferred embodiment, which is given by way of example only, with reference to the accompanying schematic drawing, in which:

FIG. 1 illustrates a diagram of a typical wireless dental handpiece according to the invention according to one embodiment; and FIG. 2 schematically shows a foot pedal switch associated with the dental handpiece.

As shown in FIG. 1, a dental handpiece, comprises an electrical motor 10 which can be sealed or detachable. For example, the dimension of the electrical motor 10 can be between 15 mm-20 mm in width and 40-50 mm in length and can be located within the detachable handpiece body in the outer sleeve 2.

The dental handpiece comprises one or several Peltier elements 5 which are received in the tip portion 4 of the handpiece and are arranged around the tool-holding socket 2, the one or several Peltier elements 5 having a cool face in thermal contact with the tool-holding socket 2 to cool a treatment tool 3 held therein when the tool 3, e.g. a burr, is driven in rotation or oscillation.

The one or several Peltier elements 5 can have dimensions comprised between 10-15 mm, the cold side of the one or several Peltier elements 5 being in direct contact with the dental burr 3 to cool down its heating during drilling. The one or several Peltier elements 5 are powered by an electric source to produce the cooling effect with the surface of the handpiece serving as the warm side of the one or several Peltier elements 5.

The components of the handpiece are covered by thermal insulation material, for example foams, insulating plastics, solid material, rubber sponge or similar.

Two tubes 8, 9 extending through the outer sleeve 1, one for lubricant material and the other for compressed gas, for example compressed air, CO2, or an electric motor producing air pressure, are used to produce a fluid jet or a spray effect for the lubricant material. The tubes 8, 9 terminate in nozzle chambers 6 having a discharge orifices that can continuously spray high viscous liquid for delivering the lubricant to the cutting site, namely the tool 3.

A WiFi chipset 11 located in the shank of the handpiece sleeve 1 receives orders from a foot pedal switch 12 associated with the handpiece, and is directly connected with a digital handpiece control.

The dental handpiece also comprises a light source 7 in the tip portion 4 of the handpiece. The light source 7 can be for example an optical fiber and can be integrated in the handpiece or attached to it.

Due to the cooling effect of the one or several Peltier elements 5, the dental handpiece according to the invention offers an anti-bacterial effect during the dental treatment when blood is exposed especially during endodontic, surgical and implant treatment.

LEGEND

1—Outer sleeve
2—tool-holding socket
3—treatment tool
4—tip portion of the handpiece
5—Peltier element
6—nozzle chambers
7—light source
8—tubes
9—tubes
10—motor
11—wifi chipset
12—pedal switch

The invention claimed is:

1. A dental handpiece, comprising an outer sleeve (1), a tool-holding socket (2) for holding a treatment tool (3) arranged in the handpiece, wherein the tool-holding socket (2) has a central axis about which the tool-holding socket (2) can be rotated and/or oscillated and wherein the tool-holding socket (2) is arranged to be driven by a driveshaft of the handpiece driven by a motor (10) housed in said outer sleeve (1), characterized in that at least one Peltier element (5) is received in the handpiece in thermal contact with the tool-holding socket (2), the Peltier element (5) having a cool face in thermal contact with the tool-holding socket (2) to cool a treatment tool (3) held therein when the tool (3) is driven in rotation or oscillation.

2. A dental handpiece according to claim 1, wherein the motor (10) is an electric motor driven by a power supply and/or a battery.

3. A dental handpiece according to claim 1, comprising two tubes (8, 9) external or internal to the outer sleeve (1), one for lubricant and the other one for compressed gas or for pumped liquid/gas, the two tubes (8, 9) terminating with discharge nozzles for delivering sprayed lubricant to a tool (3) held in the handpiece.

4. A dental handpiece according to claim 1, comprising a wireless receiver (11) housed in the outer sleeve (1) of the handpiece and arranged for digital handpiece control and for a wireless connection with an external control (12).

5. A dental handpiece according to claim 4, wherein said external control (12) comprises a foot pedal containing a transmitter, or a PC, or a smart phone, a smart tablet, a PC, or a laptop.

6. A dental handpiece according to claim 1, wherein the outer sleeve (1) constitutes a handpiece body with a resistant surface coating.

7. A dental handpiece according to claim 6, comprising a thermal insulation material covering the surface of a handpiece body.

8. A dental handpiece according to claim 1, wherein the tool-holding socket (2) houses a detachable handpiece shank and head adapted to receive different dental treatment tools (3).

9. A dental handpiece according to claim 1, comprising a light source (7) located in or attached to a tip portion (4) of the handpiece.

10. A dental handpiece according to claim 1, which includes a micro cryocooler and/or micro gas circulation within the handpiece outer sleeve (1) for cooling purposes.

11. A dental handpiece according to claim 1, wherein the tool-holding socket (2)- and the Peltier element (5) are located in a tip portion (4) of the handpiece.

12. A dental handpiece according to claim 11, wherein a light source (7) is also located in the tip-portion of the handpiece.

13. A dental handpiece according to claim 1, comprising a fixed and/or removable screen arranged on the outer sleeve (1) of the handpiece, the screen being arranged to show the status of the handpiece including its battery status, its speed and lubricant flow.

* * * * *